(12) United States Patent
Gruter

(10) Patent No.: US 8,231,693 B2
(45) Date of Patent: Jul. 31, 2012

(54) 5-SUBSTITUTED 2-(ALKOXYMETHYL)FURANS

(75) Inventor: Gerardus Johannes Maria Gruter, Heemstede (NL)

(73) Assignee: Furanix Technologies B.V. (NL)

( * ) Notice: Subject to any disclaimer, the term of this patent is extended or adjusted under 35 U.S.C. 154(b) by 213 days.

(21) Appl. No.: 12/594,189

(22) PCT Filed: Sep. 5, 2008

(86) PCT No.: PCT/EP2008/007423
§ 371 (c)(1),
(2), (4) Date: Jan. 13, 2010

(87) PCT Pub. No.: WO2009/030509
PCT Pub. Date: Mar. 12, 2009

(65) Prior Publication Data
US 2011/0302826 A1 Dec. 15, 2011

(30) Foreign Application Priority Data

Sep. 7, 2007 (EP) .................................. 07075777
May 19, 2008 (EP) .................................. 08075504

(51) Int. Cl.
*C10L 1/185* (2006.01)
*C07D 307/42* (2006.01)
(52) U.S. Cl. ........................... 44/350; 549/497; 549/502
(58) Field of Classification Search .................. 549/497, 549/502; 44/350
See application file for complete search history.

(56) References Cited

U.S. PATENT DOCUMENTS

| 5,491,180 A * | 2/1996 | Kiuchi et al. ................ 523/139 |
| 2002/0053161 A1 | 5/2002 | Lacome |

FOREIGN PATENT DOCUMENTS

| DE | 25 26 198 A1 | 1/1976 |
| EP | 0 082 689 A | 6/1983 |
| EP | 0 669 163 A | 8/2005 |
| FR | 2 679 918 A | 2/1993 |

OTHER PUBLICATIONS

Synthesis and Characterisation of some 1,4,8,11,15,18,22,25-Octa(alkoxymethyl)-phthalocyanines: a New Series of Discotic liquid Crystals by A.N. Cammidge et al. Journal of the Chemical Society Perkin Transations 1, vol. 12, 1991, pp. 3053-3058.*
Tetrahedron Letters vol. 22 No. 15 (1981) pp. 1443-1446 by Ben L Feringa.*
Ben L. Feringa: Tetrahedron Letters, vol. 22, No. 15, 1981, pp. 1443-1446.
A. N. Cammidge et al: Journal of the Chemical Society Perkin Transactions 1, vol. 12, 1991, pp. 3053-3058.
Y. Roman-Leshkov et al: Nature, vol. 447, Jun. 21, 2007, pp. 982-986.
R. S. Rao et al: Catalysis Letters, vol. 60, 1999, pp. 51-57.

* cited by examiner

*Primary Examiner* — Bernard Dentz
(74) *Attorney, Agent, or Firm* — Barry L. Davison; Davis Wright Tremaine LLP

(57) ABSTRACT

The present invention concerns a method for the manufacture of a 5-substituted 2-(alkoxymethyl)furan (or a mixture of such furans) by reacting a starting material comprising at least a 5-substituted furfural with hydrogen in the presence of an alcohol and a catalyst system.

23 Claims, No Drawings

United States Patent US 8,231,693 B2

5-SUBSTITUTED 2-(ALKOXYMETHYL)FURANS

CROSS-REFERENCE TO RELATED APPLICATIONS

This application is the United States nationalization, under 35 U.S.C. §371, of International Application No. PCT/EP2008/007423, filed 05 Sep. 2008, which claims the benefit of priority to European Patent Application Serial Nos. 07075777.8 filed 07 Sep. 2007, and 08075504.4 filed 19 May 2008, all of which are incorporated by reference herein in their entirety.

TECHNICAL FIELD

The present invention concerns a method for the manufacture of a 5-substituted 2-(alkoxymethyl)furan (or a mixture of such furans) by reacting a starting material comprising at least a 5-substituted furfural with hydrogen in the presence of an alcohol and a catalyst system. The invention also concerns a method for the manufacture of mixtures of 5-substituted 2-(alkoxymethyl)furan(s) and 2-(alkoxymethyl)furan(s) by reacting a starting material further comprising furfural. The invention also concerns the use of the products or product mixtures obtained by the method according to the invention as a fuel or a fuel additive. The invention also relates to the use of 2-(alkoxymethyl)furan(s) as a fuel or fuel additive.

BACKGROUND ART

Fuel, fuel additives and various chemicals used in the petrochemical industry are derived from oil, gas and coal, all finite sources. Biomass, on the other hand, is considered a renewable source. Biomass is biological material (including biodegradable wastes) which can be used for the production of fuels or for industrial production of e.g. fibres, chemicals or heat. It excludes organic material which has been transformed by geological processes into substances such as coal or petroleum.

Production of biomass derived products for non-food applications is a growing industry. Bio-based fuels are an example of an application with strong growing interest. Biomass contains sugars (hexoses and pentoses) that may be converted into value added products. Current biofuel activities from sugars are mainly directed towards the fermentation of sucrose or glucose into ethanol or via complete breakdown via Syngas to synthetic liquid fuels. EP 0641 854 describes the use of fuel compositions comprising of hydrocarbons and/or vegetable oil derivatives containing at least one glycerol ether to reduce particulate matter emissions.

More recently, the acid catalysed reaction of fructose has been re-visited, creating HMF as an intermediate of great interest. Most processes investigated have the disadvantage that HMF is not very stable at the reaction conditions required for its formation. Fast removal from the water-phase containing the sugar starting material and the acid catalyst has been viewed as a solution for this problem. Researchers at the University of Wisconsin-Madison have developed a process to make HMF from fructose. HMF can be converted into monomers for plastics, petroleum or fuel extenders, or even into fuel itself. The process by prof. James Dumesic and co-workers first dehydrates the fructose in an aqueous phase with the use of an acid catalyst (hydrochloric acid or an acidic ion-exchange resin). Salt is added to salt-out the HMF into the extracting phase. The extracting phase uses an inert organic solvent that favors extraction of HMF from the aqueous phase. The two-phase process operates at high fructose concentrations (10 to 50 wt %), achieves high yields (80% HMF selectivity at 90% fructose conversion), and delivers HMF in a separation-friendly solvent (DUMESIC, James A, et al. "Phase modifiers promote efficient production of Hydroxymethylfurfural from fructose". Science. 30 Jun. 2006, vol. 312, no. 5782, p. 1933-1937). Although the HMF yields from this process are interesting, the multi-solvent process has cost-disadvantages due to the relatively complex plant design and because of the less than ideal yields when cheaper and less reactive hexoses than fructose, such as glucose or sucrose, are used as a starting material. HMF is a solid at room temperature which has to be converted in subsequent steps to useful products. Dumesic has reported an integrated hydrogenolysis process step to convert HMF into dimethylfuran (DMF), which is assumed to be an interesting gasoline additive.

In WO 2006/063220 a method is provided for converting fructose into 5-ethoxymethylfurfural (EMF) at 60° C., using an acid catalyst either in batch during 24 hours or continuously via column elution during 17 hours. Applications of EMF were not discussed. Also in copending patent application PCT/EP2007/002145 the manufacture of HMF ethers are described, including the use of such ethers as fuel or fuel additive. Indeed, both the methyl ether and the ethyl ether (methoxymethylfurfural, or MMF; ethoxyethylfurfural or EMF) were prepared and tested. A similar case is co-pending patent application PCT/EP2007/002146, which describes the manufacture of HMF esters, such as acetylmethylfurfural (AMF).

Moreover, it is known to make furfural from the polysaccharide hemicellulose, a polymer of sugars containing five carbon atoms each. When heated with sulphuric acid, hemicellulose undergoes hydrolysis to yield these sugars, principally xylose. Under the same conditions of heat and acid, xylose and other five carbon sugars undergo dehydration, losing three water molecules to become furfural:

$C_5H_{10}O_5 \rightarrow C_5H_4O_2 + 3H_2O$

Although MMF, EMF, AMF and other ethers and esters of HMF and furfural are useful as fuel or fuel additives, the inventors found that these ethers and esters leave room for improvement, in particular when used in higher concentration blends with fuels such as gasoline, kerosene, diesel, biodiesel or green diesel. The inventors have therefore set out to overcome this shortfall. It is known that HMF may be converted into 2,5-dimethylfuran. For instance, in "Production of dimethylfuran for liquid fuels from biomass-derived carbohydrates", Nature, vol. 447 (21 Jun. 2007), pp. 982-985, James Dumesic et al. describes the conversion of fructose into HMF, which is subsequently converted into several hydrogenation steps via 2,5-dihydroxymethylfuran and 2-methyl-5-hydroxymethylfuran into DMF. Thus, a large amount of hydrogen is required to generate a liquid fuel suitable for the transportation sector.

Surprisingly, the current inventors found that the conversion of HMF into DMF is not required in order to prepare a product with a high energy density, suitable boiling point and suitable solubility. Moreover, suitable fuel or fuel additives may even be made from furfural, HMF, HMF ethers and HMF esters such as EMF and AMF and/or mixtures containing these components with much smaller amounts of hydrogen and without losing molecular mass but with adding molecular mass to the products. This would therefore provide a route to an alternative fuel or fuel additive from a renewable (and hence CO2 neutral) source.

DISCLOSURE OF INVENTION

Accordingly, the current invention provides a method for the manufacture of ethers of 5-substituted furfural via the corresponding alcohol by reacting 5-substituted furfural with hydrogen in the presence of an alcohol and a catalyst system, comprising of one or more catalysts. Within the scope of the current invention is the use of 5-substituted furfural, and in particular 5-hydroxymethylfurfural and the ethers or esters thereof, which may be obtained from C6 sugars. The synthesis of furfural (from C5 sugars) and/or of the 5-substituted furfural are not part of the current invention. It is noted, however, that the current process is ideally suitable for the manufacture of fuel components or additives from feed containing 5-substituted furfural and optionally unsubstituted furfural, which in turn was obtained from a pentose and hexose containing biomass source. The current invention relates also to the use of 2-alkoxymethyl furan as a fuel or fuel additive, which may be obtained from furfural (pure or in a mixture as described herein elsewhere), hydrogen, alcohol in the presence of a catalyst.

When the reaction product of the above method is used as such or when it is used as an intermediate for a subsequent conversion, the selectivity of the reaction is preferably high as the product is preferably pure. However, when the reaction product of the above method is used as a fuel, a fuel additive or as a fuel or a fuel additive intermediate, the reaction product does not necessarily need to be pure. Indeed, in the preparation of fuel and fuel additives from biomass, which in itself is a mixture of various pentoses and hexoses is an advantage. Next to the 5-substituted 2-(alkoxymethyl)furan and 2-(alkoxymethyl)furan, the reaction product may contain additional non-interfering components such as levulinic acid derivatives and/or products of non-selective hydrogenation such as 5-substituted 2-methylfuran, 2-methylfuran, dimethylfuran, tetrahydrofuran derivatives and the like. For ease of reference, however, the method and the reaction product of the current invention are described in terms of the reaction of a 5-substituted furfural starting material to the di-ether 5-substituted 2-(alkoxymethyl)furan. Also within the scope of the invention is the reaction of HMF and mixtures of HMF and HMF ethers or esters which may contain furfural with hydrogen in the presence of an alcohol and a catalyst system, since HMF is believed to be produced as intermediate from the fructose and/or glucose-containing starting material during the synthesis of HMF ethers and esters.

The current invention also provides for the use of the reaction product made according to the present invention as fuel or as fuel additive. Fuels for blending with the product of the present invention include but are not limited to gasoline and gasoline-ethanol blends, kerosene, diesel, biodiesel (refers to a non-petroleum-based diesel fuel consisting of short chain alkyl (methyl or ethyl) esters, made by transesterification of vegetable oil, which can be used (alone, or blended with conventional petrodiesel), Fischer-Tropsch liquids (for example obtained from GTL, CTL or BTL gas-to-liquids/coal-to-liquids/biomass to liquids processes), diesel-biodiesel blends and green diesel and blends of diesel and/or biodiesel with green diesel (green diesel is a hydrocarbon obtained by hydrotreating biomass derived oils, fats, greases or pyrolysis oil; see for example the UOP report OPPORTUNITIES FOR BIORENEWABLES IN OIL REFINERIES FINAL TECHNICAL REPORT, SUBMITTED TO: U.S. DEPARTMENT OF ENERGY (DOE Award Number: DE-FG36-05GO15085). The product is a premium diesel fuel containing no sulfur and having a cetane number of 90 to 100). Fuels for blending with the product of the present invention may also include one or more other furanics, wherein the expression furanics is used to include all derivatives of furan and tetrahydrofuran. The invention also provides a fuel composition comprising a fuel element as described above and the reaction product made according to the present invention.

MODE(S) FOR CARRYING OUT THE INVENTION

The synthesis of HMF from fructose, glucose and sucrose as a biomass source is a hot topic. HMF has been obtained in processes using both homogeneous and heterogeneous catalysts, using different diluent systems such as water, 2 phase systems for extracting the HMF into an organic phase after its formation, or using diluent systems such as acetone, dmso or ionic liquids.

The current method provides for the conversion of 5-substituted furfural into 5-substituted 2-(alkoxymethyl)furan and as furfural may be present when pentoses were present in the sugar dehydration step or when furfural is formed during hexose dehydration, the current method also provides for the concurrent conversion of the furfural into furfuryl alcohol and its etherification with the added alcohol. Surprisingly, little or no ethers are found derived by the etherification of the added alcohol with itself.

The alcohol used in the method of the current invention preferably bears a single hydroxyl group, which may be in a primary, secondary or even tertiary position. Diols and polyhydric compounds may be used, but provide little benefit. The alcohol may comprise from 1 to 20 carbon atoms, preferably from 1 to 8 carbon atoms. Examples include methanol, ethanol, 2-propanol, 2-butanol, 2-methyl-1-propanol (isobutanol), 2-methyl-2-propanol (tert-butanol), 2-pentanol (s-amyl alcohol); 2-methyl-1-butanol (p-amyl alcohol); 2-methyl-2-butanol (t-amyl alcohol); 3-methyl-1-butanol (isoamyl alcohol); 2,2-dimethyl-1-propanol (neopentyl alcohol); 2-hexanol; 2-ethyl-1-hexanol (isooctyl alcohol). Preferred alcohols used in the method of the current invention include methanol, ethanol, propanol, iso-propanol, isobutanol, tert-butanol, isoamyl alcohol, isooctyl alcohol. Also blends of alcohols may be used, e.g., of methanol and ethanol.

The amount of alcohol used during the manufacture of the HMF ether is preferably at least equimolar on the furfural, but typically is used in much greater access. Indeed, the alcohol may be used as solvent or co-solvent. In such a case, a sufficient amount of alcohol is present to form the furfuryl ether.

The catalyst system used in the method of the present invention may comprise one or more (co)catalysts, and preferably comprises a single catalyst having hydrogenation and etherification functionality or a combination of (a) hydrogenation catalyst(s) and (an) etherification catalyst(s), for the hydrogenation and for the etherification steps. The single catalyst may for instance be used in the form of an acidic hydrogenation catalyst, or a combination of 2 or more catalysts can be used, for the hydrogenation and for the etherification steps.

The hydrogenation catalyst (or the single hydrogenation/etherification catalyst) is preferably a heterogeneous (meaning solid) catalyst. Suitably, it is a granular catalyst which may be formed into any suitable shape, e.g. pellets, rings or saddles.

Hydrogenation catalysts for aldehydes are known and believed suitable in the method of the current invention. Typical aldehyde hydrogenation catalysts include copper-containing catalysts and Group VIII metal-containing catalysts. Examples of suitable copper-containing catalysts include copper-on-alumina catalysts, reduced copper oxide/zinc oxide catalysts, with or without a promoter, manganese promoted copper catalysts, and reduced copper chromite catalysts, with or without a promoter, while suitable Group VIII metal-containing catalysts include platinum, rhodium, ruthenium and palladium catalysts, preferably on a refractory support such as carbon, silica, alumina, aluminasilica, a carbonate such as barium carbonate, diatomaceous earth and the like.

Suitable copper oxide/zinc oxide catalyst precursors include CuO/ZnO mixtures wherein the Cu:Zn weight ratio ranges from about 0.4:1 to about 2:1. Promoted copper oxide/zinc oxide precursors include CuO/ZnO mixtures wherein the Cu:Zn weight ratio ranges from about 0.4:1 to about 2:1 which are promoted with from about 0.1% by weight up to about 15% by weight of barium, manganese or a mixture of barium and manganese. Suitable copper chromite catalyst precursors include those wherein the Cu:Cr weight ratio ranges from about 0.1:1 to about 4:1, preferably from about 0.5:1 to about 4:1. Promoted copper chromite precursors include copper chromite precursors wherein the Cu:Cr weight ratio ranges from about 0.1:1 to about 4:1, preferably from about 0.5:1 to about 4:1, which are promoted with from about 0.1% by weight up to about 15% by weight of barium, manganese or a mixture of barium and manganese. Manganese promoted copper catalyst precursors typically have a Cu:Mn weight ratio of from about 2:1 to about 10:1 and can include an alumina support, in which case the Cu:Al weight ratio is typically from about 2:1 to about 4:1. Other catalysts which can be considered for use include Pd/ZnO catalysts of the type mentioned by P. S. Wehner and B. L. Gustafson in Journal of Catalysis 136, 420-426 (1992), supported palladium/zinc catalysts of the type disclosed in U.S. Pat. No. 4,837,368 and U.S. Pat. No. 5,185,476, and chemically mixed copper-titanium oxides of the type disclosed in U.S. Pat. No. 4,929,777.

Further catalysts of interest for use in the process of the invention include the rhodium/tin catalysts reported in A. El Mansour, J. P. Candy, J. P. Bournonville, O. A. Ferrehi, and J. M Basset, Angew. Chem. 101, 360 (1989).

Any recognised supporting medium may be used to provide physical support for the catalyst used in the process of the invention. This support can be provided by materials such as zinc oxide, alumina, silica, aluminasilica, silicon carbide, zirconia, titania, carbon, a zeolite, or any suitable combination thereof. Particularly preferred are catalyst systems comprising a Group VIII metal ("noble metal") on a carbon support, since such catalysts systems may be used to perform the hydrogenation and etherification.

The acid etherification catalyst system in the method of the present invention can be selected from amongst (halogenated) organic acids, inorganic acids, Lewis acids, ion exchange resins and zeolites or combinations and/or mixtures thereof. It may be a homogeneous catalyst, but heterogeneous catalysts are preferred for purification reasons. The HMF ethers can be produced with a protonic, Brønsted or, alternatively, a Lewis acid or with catalysts that have more than one of these acidic functionalities.

The protonic acid may be organic or inorganic. For instance, the organic acid can be selected from amongst oxalic acid, levulinic acid, maleic acid, trifluoro acetic acid (triflic acid), methansulphonic acid or para-toluenesulphonic acid. Alternatively, the inorganic acid can be selected from amongst (poly)phosphoric acid, sulphuric acid, hydrochloric acid, hydrobromic acid, nitric acid, hydroiodic acid, optionally generated in situ.

Certain salts may be used as catalyst, wherein the salt can be any one or more of $(NH_4)_2SO_4/SO_3$, ammonium phosphate, pyridinium chloride, triethylamine phosphate, pyridinium salts, pyridinium phosphate, pyridinium hydrochloride/hydrobromide/perbromate, DMAP, aluminium salts, Th and Zr ions, zirconium phosphate, Sc and lanthanide ions such as Sm and Y as their acetate or trifluoroactate (triflate) salt, Cr-, Al-, Ti-, Ca-, In-ions, $ZrOCl_2$, $VO(SO_4)_2$, $TiO_2$, V-porphyrine, Zr-, Cr-, Ti-porphyrine.

Lewis acids selected as dehydration catalyst can be any one of $ZnCl_2$, $AlCl_3$, $BF_3$. Ion exchange resins can be suitable dehydration catalysts. Examples include Amberlite™ and Amberlyst™, Diaion™ and Levatit™. Other solid catalyst that may be used include natural clay minerals, zeolites, supported acids such as silica impregnated with mineral acids, heat treated charcoal, metal oxides, metal sulfides, metal salts and mixed oxides and mixtures thereof. If elevated reactions temperatures are used, as defined hereafter, then the catalyst should be stable at these temperatures.

An overview of catalysts that may be used in the method of the current invention may be found in Table 1 of the review article prepared by Mr. Lewkowski: "Synthesis, chemistry and applications of 5-hydroxymethylfurfural and its derivatives" Arkivoc. 2001, p. 17-54. The amount of catalyst may vary, depending on the selection of catalyst or catalyst mixture. For instance, the catalyst can be added to the reaction mixture in an amount varying from 0.01 to 40 mole % drawn on the (substituted) furfural content of the feed, preferably from 0.1 to 30 mole %, more preferably from 1 to 20 mole %.

In the preferred embodiment, the catalyst is a heterogeneous catalyst.

The temperature at which the reaction is performed may vary, but in general it is preferred that the reaction is carried out at a temperature from 0 to 200 degrees Celsius, preferably from 10 to 150 degrees Celsius, more preferably from 20 to 120 degrees Celsius. Also, the hydrogenation reaction is most selective at low temperatures such as e.g. between 20 and 80 degrees Celsius, depending on the selected catalyst. The reaction of the invention can also be carried out in a system with 2 reactors in series, whereby the hydrogenation step and the etherification step are carried out in the first and second reactor at lower and higher temperature, respectively. The reaction may be performed in a single reactor, at a temperature from 20 to 140 degrees Celsius, or in two reactors, where in the first reactor the hydrogenation is performed at a temperature from 20 to 80 degrees Celsius, and where in the second reactor the hydrogen is removed for the etherification at a temperature from 40 to 160 degrees Celsius, preferably from 60 to 120 degrees Celsius. The operation in one batch reactor can start with a low temperature hydrogenation, followed by increasing the temperature and removing the hydrogen gas.

Hydrogen is supplied is sufficient abundance, and either bubbled through the reaction medium introduced concurrently or counter currently with one of the feed streams or dissolved using another form of mixing. Depending on the catalyst and the selected process temperature, the reaction is carried out at a hydrogen pressure from 1 to 100 bars, preferably from 2 to 25 bars, more preferably from 2 to 10 bars. In general, pressures higher than 100 bars are less preferred as the selectivity of the reaction reduces and too much hydrogen is consumed for by-products formation.

The furfural, HMF and HMF ether and ester containing starting material is typically dissolved in a solvent or more preferably in the alcohol reactant, in order to facilitate the reaction. The non-alcohol solvent may be selected form the group consisting of organic solvents such as, ketones, ethers, alkanes and the like.

The alcohol solvent is the alcohol selected for the etherification. The amount of solvent is preferably sufficient to dissolve or suspend the starting material and to prevent certain side-reactions.

The method of the current invention may be carried out in a batch process or in a continuous process, with or without recycle of (part of) the product stream to control the reaction temperature (recycle via a heat exchanger). For instance, the method of the invention can be performed in a continuous flow process. In such method, one or two homogenous catalysts may be used and the residence time of the reactants in the flow process is between 0.1 second and 10 hours, preferably from 1 second to 1 hours, more preferably from 5 seconds to 20 minutes.

Alternatively, the continuous flow process may be a fixed bed continuous flow process or a reactive (catalytic) distillation process with a heterogeneous acid catalyst. To initiate or regenerate the heterogeneous acid catalyst or to improve performance, or when a heterogeneous hydrogenation catalyst is used in combination with a homogeneous acidic etherification catalys, an inorganic or organic acid may be added to the feed of the fixed bed or reactive distillation continuous flow process. In a fixed bed process, the liquid hourly space velocity (LHSV) can be from 1 to 1000, preferably from 5 to 500, more preferably from 10 to 250 and most preferably from 25 to 100 $min^{-1}$.

The above process results in stable furan ethers, which can then be used as such or be converted into a further derivative before being used as fuel and/or as fuel additive. The inventors are of the opinion that some of the products prepared by the method of the current invention are actually new. Thus, the ethers made from alkoxymethylfurfural with C1 to C20 alcohols, preferably C1 to C8 alcohols are new and are excellent fuel components or fuel additives. Since these alcohols may be made from biomass, this might open a class of products that are fully biomass-derived. Accordingly, these new ethers are claimed as well.

The HMF ethers of the invention can also be used as or can be converted to compounds that can be used as solvent, as monomer in a polymerization (such as 2,5-furan dicarboxylic acid or FDCA), as fine chemical or pharmaceutical intermediate, or in other applications. Oxidation of the HMF ethers using an appropriate catalyst under appropriate conditions such as for example described for p-xylene with a NHPI/Co $(OAc)_2/MnOAc)_2$ catalyst system in Adv. Synth. Catal. 2001, 343, 220-225 or such as described for HMF with a Pt/C catalyst system at pH<8 in EP 0 356 703 or such as described for HMF with a Pt/C catalyst system at pH>7 in FR 2 669 634, all with air as an oxidant, resulted in the formation of 2,5-Furan dicarboxylic acid (FDCA).

The invention further concerns the use of the HMF ethers prepared by the method of the current invention as fuel and/or as fuel additive. Of particular interest is the use of the ethers in diesel, biodiesel or "green diesel", given its (much) greater solubility therein than ethanol. Conventional additives and blending agents for diesel fuel may be present in the fuel compositions of this invention in addition to the above mentioned fuel components. For example, the fuels of this invention may contain conventional quantities of conventional additives such as cetane improvers, friction modifiers, detergents, antioxidants and heat stabilizers, for example. Especially preferred diesel fuel formulations of the invention comprise diesel fuel hydrocarbons and HMF ether as above described together with peroxidic or nitrate cetane improvers such as ditertiary butyl peroxide, amyl nitrate and ethyl hexyl nitrate for example.

Examples are enclosed to illustrate the method of the current invention and the suitability of the products prepared therefrom as fuel. The examples are not meant to limit the scope of the invention.

EXAMPLE 1

Formation of 2,5-di(ethoxymethyl)furan

In a 7.5 ml batch reactor, 0.06 mmol 5-(ethoxymethyl) furfural (EMF) in ethanol/$H_2O$ (90/10) and 3.3 mmol $H_2$ was reacted for 2 hours at a temperature of 150 or 80 degrees Celsius with 5 mg heterogeneous hydrogenation catalyst and in some cases with 5 mg acid catalyst. Four furan peaks were observed in the UV spectrum. Mass spectrometry (LC-MS Cl) identified these products as 5-(ethoxymethyl)furfural (EMF; starting material), 2,5-di(ethoxymethyl)furan (DEMF), 2-(ethoxymethyl)-5-(hydroxymethyl)furan (EMHMF) and 2-(ethoxymethyl)-5-methylfuran (EMMeF).

Conversion of substrate, selectivity and yield of furan derivatives were calculated according to the following formulae:

$$X = 100 * m_{r\ substrate}/m_{0\ substrate}$$

| | |
|---|---|
| X | conversion (%) |
| $m_{r\ substrate}$ | amount of reacted substrate (mg) |
| $m_{0\ substrate}$ | amount of substrate in feed (mg) |

$$S_{compound} = 100 * n_{r\ substrate}/n_{0\ substrate}$$

| | |
|---|---|
| $S_{compound}$ | selectivity to compound (%) |
| $n_{r\ substrate}$ | moles of substrate reacted |
| $n_{0\ substrate}$ | moles of substrate in feed |

$$Yield = 100 * n_{product}/n_{0\ substrate}$$

| | |
|---|---|
| Yield | yield (%) |
| $n_{product}$ | moles of product formed |

Selectivities and conversions for catalysts used in this example can be found in table below.

TABLE 1

Conversion and selectivities for the hydrogenation of 5-(ethoxymethyl)furfural in the presence of ethanol at different temperatures and reaction times.

| Catalyst 1 | Catalyst 2 | T [° C.] | Conversion [%] | sEMHMF [%] | sDEMF [%] | sEMMeF [%] | sEMHMF + DEMF [%] | s Further hydrogenate products [%] |
|---|---|---|---|---|---|---|---|---|
| 1.85% Ru on silica | None | 80 | 29.0 | 92.5 | 0.1 | 0.0 | 92.6 | 7.4 |
| 1.85% Ru on silica | CrCl2 | 80 | 42.4 | 13.8 | 28.7 | 0.2 | 42.5 | 57.3 |
| 5% Ru on alumina | None | 150 | 92.4 | 52.5 | 0.2 | 0.0 | 52.7 | 47.3 |
| 5% Ru on alumina | None | 80 | 73.3 | 85.0 | 0.8 | 0.1 | 85.8 | 14.2 |
| 5% Ru on alumina | Amberlyst36Wet | 80 | 91.1 | 33.1 | 27.7 | 0.4 | 60.8 | 38.9 |
| 5% Ru on alumina | CrCl2 | 80 | 70.8 | 15.9 | 28.5 | 0.3 | 44.3 | 55.4 |
| 5% Pt/0.5% V | None | 80 | 99.5 | 65.5 | 5.2 | 3.6 | 70.7 | 25.8 |

TABLE 1-continued

Conversion and selectivities for the hydrogenation of 5-(ethoxymethyl)furfural in the presence of ethanol at different temperatures and reaction times.

| Catalyst 1 | Catalyst 2 | T [° C.] | Conversion [%] | sEMHMF [%] | sDEMF [%] | sEMMeF [%] | sEMHMF + DEMF [%] | s Further hydrogenate products [%] |
|---|---|---|---|---|---|---|---|---|
| 5% Pt/0.5% V | CrCl2 | 80 | 70.7 | 13.0 | 21.8 | 3.4 | 34.8 | 61.9 |
| 5% Rh on active C | Bentonite | 80 | 66.9 | 32.4 | 6.3 | 7.9 | 38.7 | 53.4 |
| Ni on silica | None | 150 | 93.2 | 33.0 | 0.1 | 0.8 | 33.2 | 66.1 |
| Ni on silica | None | 80 | 98.6 | 51.1 | 0.0 | 0.0 | 51.1 | 48.9 |
| Ni on silica | Amberlyst36Wet | 80 | 99.3 | 22.3 | 21.5 | 0.1 | 43.8 | 56.2 |
| Ni on silica | CrCl2 | 80 | 31.0 | 98.5 | 0.7 | 0.5 | 99.2 | 0.3 |

Analytical Method

The reaction products were quantified with the aid of HPLC-analysis with an internal standard (saccharine, Sigma Aldrich). An Agilent 1100 series chromatograph, equipped with UV and ELSD detectors, was used. Stationary phase was reverse phase C18 (Sunfire 3.5 μm, 4.6×100 mm, Waters) column. A gradient elution at a constant flow 0.6 ml/min and temperature 40° C. was used according to the following scheme.

| Time | H2O (vol %) | MeOH (vol %) | MeCN (vol %) | Flow (ml/min) | T (C.) |
|---|---|---|---|---|---|
| Initial | 95 | 0 | 5 | 1 | 40 |
| 1 | 89 | 3 | 8 | 1 | 40 |
| 8 | 25 | 3 | 72 | 1 | 40 |

C.I. Mass spectrum of DEMF (MW=184.2 g/mol)

EXAMPLE 2

Batch Experiment with Hydrogenation/Etherification of 5-(ethoxymethyl)furfural

In a 7.5 ml batch reactor, 0.06 mmol 5-(ethoxymethyl) furfural (EMF) in 1 mL ethanol and 5 bars of hydrogen was reacted with 3 mol % of a Pt/C catalyst for 4 days at room temperature. The starting material was completely converted in 100% selectivity to 5-(ethoxymethyl)-2-hydroxymethyl) furan. Subsequently, the mixture was heated to 75° C. for 1 day without hydrogen. The 5-(ethoxymethyl)-2-hydroxymethyl)furan was fully converted and 2,5-bis(ethoxymethyl) furan was obtained in 80% yield. 20% Side products are ring opened levulinate derivatives. The experiment was successfully repeated on a 20 gram scale.

EXAMPLE 3

Batch Experiment with Hydrogenation/Etherification of 5-(tert-butoxymethyl)furfural In a 7.5 ml batch reactor, 0.06 mmol 5-(tert-butoxymethyl) furfural (tBMF) in 1 mL ethanol and 2 bars of hydrogen was reacted with 3 mol % of a 5% Rh on alumina catalyst for 4 hours at room temperature. The starting material was completely converted in 100% selectivity to 5-(tertbutoxymethyl)-2-(ethoxymethyl)furan. The experiment was successfully repeated on a 20 gram scale.

No reduction of the furan ring could be detected.

EXAMPLE 4

Batch Experiment with Hydrogenation/Etherification of 5-(hydroxymethyl)furfural

In a 7.5 ml batch reactor, 0.06 mmol 5-(hydroxymethyl) furfural (HMF) in 1 mL ethanol and 5 bars of hydrogen was reacted with 3 mol % of a Pt/C catalyst for 2 days at room temperature. The starting material was completely converted in 100% selectivity to 2,5-di(hydroxymethyl)furan. Subsequently, the mixture was heated to 75° C. for 1 day without hydrogen. The 2,5-di(hydroxymethyl)furan was fully converted and 2,5-bis(ethoxymethyl)furan was obtained in 75% yield. 25% Side products are ring opened levulinate derivatives. The experiment was successfully repeated on a 20 gram scale.

EXAMPLE 5

Diesel Fuel Applications

Fuel Solubility

Fuel solubility is a primary concern for diesel fuel applications. Not all highly polar oxygenates have good solubility in the current commercial diesel fuels. Results show that 2,5-di(ethoxymethyl)furan and 5-(tertbutoxymethyl)-2-(ethoxymethyl)furan are miscible in all blend ratio's with commercial diesel. In a comparative set of experiments it was shown that ethoxymethylfurfural (EMF) is completely miscible in a 5 vol % blend with commercial diesel, but that phase separation occurs with the 25 vol % and with the 40 vol % blends of EMF and diesel.

EXAMPLE 6

5-substituted 2-(alkoxymethyl)furans

A teflon lined, 7.5 mL stainless steel batch reactor containing 350 mq (2.3 mmol) of 5-(ethoxymethyl)furfural in 0.5 mL methanol, a hydrogenation catalyst (Ni on Silica) and an etherification catalyst (zeolite β-SAR 75) was pressurized to 12.5 bar with hydrogen and subsequently heated, under stirring, to 100° C. for 3 hours. After the reaction, de reactor is cooled quickly in an ice bath and depressurized. A sample is diluted with methanol and analysed of the products with GC and GC-MS. The results are shown in the below Table.

In this experiment, the selectivity was calculated slightly different, based on the formula:

Selectivity=$100*n_t(\text{product})/[n_0(\text{substrate})-n_t(\text{substrate})]$ Where:
$n_0$—the initial number of moles
$n_t$—the number the moles of a compound at time "t".

TABLE 1

Hydrogenation/etherification of EMF in MeOH to EMF alcohol and ethers

| Cat. 1 | Cat. 1 [mg] | Cat. 2 | Cat. 2 [mg] | Conversion [%] | S-EMHMF [%] | S-DMMF [%] | S-EMMeF [%] | S-DMMF + EMMeF [%] |
|---|---|---|---|---|---|---|---|---|
| Ni on silica | 50 | Zeolite Beta (SAR 75) | 50 | 92 | 3.8 | 47.9 | 30.1 | 78.0 |
| Ni on silica | 10 | Zeolite Beta (SAR 75) | 10 | 37 | 7.9 | 46.7 | 36.0 | 82.7 |

EXAMPLE 7

5-substituted 2-(alkoxymethyl)furans using a mixture of EMF and Furfural

Example 6, was repeated with 180 mq (1.9 mmol) of furfural and 180 mq (1.2 mmol) 5-(ethoxymethyl)furfural in 0.48 mL methanol. The batch reactor was pressurized to 20 bar of hydrogen and subsequently heated, under stirring, to 100° C. for 2 hours. The results are shown in Table 2.

TABLE 2

Hydrogenation/etherification of Furfural and EMF in MeOH

| Cat. 1 | Cat. 1 [mg] | Cat. 2 | Cat. 2 [mg] | Conversion [%] | S-EMHMF [%] | S-DMMF [%] | S-EMMeF [%] | F—OH | F—OMe |
|---|---|---|---|---|---|---|---|---|---|
| Ni on silica | 20 | Zeolite Beta (SAR 75) | 20 | (EMF) 31.6 (F) 64.7 | 24 | 6.3 | 36.5 | 32.3 | 29.7 |

References
DUMESIC, James A, et al. "Phase modifiers promote efficient production of Hydroxymethylfurfural from fructose". Science. 30 Jun. 2006, vol. 312, no. 5782, p. 1933-1937.
WO 2006/063220
Chapter 15 of Advanced Organic Chemistry, by Jerry March, and in particular under reaction 5-4. (3$^{rd}$ ed., © 1985 by John Wiley & Sons, pp. 684-685).
LEWKOWSKI, Jaroslaw. Synthesis, chemistry and applications of 5-hydroxymethylfurfural and its derivatives. Arkivoc. 2001, p. 17-54.
MOREAU, Claude, et al. "Dehydration of fructose and sucrose into 5-hydroxymethylfurfural in the presence of 1-H-3-methyl imidazolium chloride acting both as solvent and catalyst", Journal of Molecular Catalysis A: Chemical 253 (2006) p. 165-169.
EP 0641 854
UOP report OPPORTUNITIES FOR BIORENEWABLES IN OIL REFINERIES FINAL TECHNICAL REPORT, SUBMITTED TO: U.S. DEPARTMENT OF ENERGY (DOE Award Number: DE-FG36-05GO15085))
Adv. Synth. Catal. 2001, 343, 220-225
EP 0 356 703
FR 2 669 634
P. S. Wehner and B. L. Gustafson in Journal of Catalysis 136, 420-426 (1992)
A. El Mansour, J. P. Candy, J. P. Bournonville, O. A. Ferrehi, and J. M Basset, Angew. Chem. 101, 360 (1989).

U.S. Pat. No. 4,837,368
U.S. Pat. No. 5,185,476
U.S. Pat. No. 4,929,777.

The invention claimed is:

1. A method for the manufacture of a 5-substituted 2-(alkoxymethyl)furan, comprising reacting a starting material comprising at least one 5-substituted furfural, and optionally further comprising further furfural, with hydrogen in the presence of an alcohol and a catalyst system.

2. Method according to claim 1, wherein the alcohol comprises from 1 to 20 carbon atoms.

3. Method according to claim 1, wherein the alcohol is selected from the group consisting of methanol, ethanol, 2-propanol, 2-butanol, 2-methyl-1-propanol (isobutanol), 2-methyl-2-propanol (tert-butanol), 2-pentanol (s-amyl alcohol); 2-methyl-1-butanol (p-amyl alcohol); 2-methyl-2-butanol (t-amyl alcohol); 3-methyl-1-butanol (isoamyl alcohol); 2,2-dimethyl-1-propanol (neopentyl alcohol); 2-hexanol; 2-ethyl-1-hexanol (isooctyl alcohol) and a blend of from two or more of the above alcohols.

4. Method according to claim 1 or 2, wherein the catalyst system comprises a heterogeneous acid hydrogenation catalyst.

5. Method according to claim 4, wherein the heterogeneous acid hydrogenation catalyst comprises at least one noble metal on a carbon support.

6. Method according to claim 1 or 2, wherein the catalyst system comprises of two catalysts, one being a hydrogenation catalyst and the other being an etherification catalyst.

7. Method according to any one of claims 1 to 3, wherein the reaction is performed in a single reactor, at a temperature from 20 to 140 degrees Celsius, or in two reactors, where in the first reactor the hydrogenation is performed at a temperature from 20 to 80 degrees Celsius, and where in the second reactor the hydrogen is removed for the etherification at a temperature from 40 to 160 degrees Celsius, wherein the operation in one batch reactor can start with a low temperature hydrogenation, followed by increasing the temperature and removing the hydrogen gas.

8. Method according to any one of claims 1 to 3, wherein the starting material is at least one selected from the group consisting of 5-(hydroxymethyl)furfural and ethers and esters of 5-(hydroxymethyl)furfural, and optionally further comprising furfural.

9. Method according to claim 8, wherein the starting material comprises 5-(hydroxymethyl)furfural.

10. Method according to any one of claims 1 to 3, wherein a solvent or solvent mixture is used, and wherein the solvent or solvents are selected from the group consisting of ketones, ethers, alkanes and aromatic hydrocarbons and mixtures thereof.

11. Method according to any one of claims 1 to 3, wherein a solvent or solvent mixture is used, and wherein the solvent is the alcohol.

12. Method according to any one of claims 1 to 3, wherein the method is performed in a continuous flow process.

13. Method according to claim 12, wherein the residence time in the flow process is between 0.1 second and 10 hours.

14. Method according to claim 13, wherein the continuous flow process is a fixed bed continuous flow process.

15. Method according to claim 14, wherein the fixed bed comprises a heterogeneous acid catalyst.

16. Method according to claim 15, wherein the continuous flow process is a reactive distillation or a catalytic distillation process.

17. Method according to claim 16, wherein in addition to a heterogeneous acid catalyst, an inorganic or organic acid catalyst is added to the feed of the fixed bed or catalytic distillation continuous flow process.

18. Method according to claim 14, comprising a liquid hourly space velocity ("LHSV") from 1 to 1000.

19. 5-(tertbutoxymethyl)-2-(methoxymethyl)furan.

20. 5-(tertbutoxymethyl)-2-(ethoxymethyl)furan.

21. 5-(2-butoxymethyl)-2-(methoxymethyl)furan.

22. A fuel or fuel composition comprising at least one ether selected from the group consisting of 5-(tertbutoxymethyl)-2-(methoxymethyl)furan, 5-(tertbutoxymethyl)-2-(ethoxymethyl)furan, and 5-(2-butoxymethyl)-2-(methoxymethyl)furan as fuel component or additive.

23. The fuel or fuel composition of claim 22, comprising at least one component selected from the group consisting of: gasoline; gasoline-ethanol blend; kerosene; diesel; a non-petroleum-based biodiesel fuel comprising a short-chain alkyl methyl or ethyl ester; Fischer-Tropsch liquid; diesel-biodiesel blend; a green diesel hydrocarbon obtained by hydrotreating biomass derived oils, fats, greases or pyrolysis oil, containing no sulfur and having a cetane number of 90 to 100; diesel-greendiesel blend; diesel-biodiesel blend; and another furanic.

* * * * *

UNITED STATES PATENT AND TRADEMARK OFFICE
CERTIFICATE OF CORRECTION

PATENT NO. : 8,231,693 B2
APPLICATION NO. : 12/594189
DATED : July 31, 2012
INVENTOR(S) : Gerardus Johannes Maria Gruter Page 1 of 1

It is certified that error appears in the above-identified patent and that said Letters Patent is hereby corrected as shown below:

In the claims at Column 12, line 24, the words "further comprising further furfural" should read "further comprising furfural".

Signed and Sealed this
Second Day of October, 2012

David J. Kappos
*Director of the United States Patent and Trademark Office*